United States Patent [19]

Oosterwaal

[11] Patent Number: 5,987,672
[45] Date of Patent: Nov. 23, 1999

[54] COMPONENTS OF A PLASTIC MATERIAL FOR USE IN A MAGNETIC RESONANCE APPARATUS

[75] Inventor: Lambertus J.M.P. Oosterwaal, Eindhoven, Netherlands

[73] Assignee: U.S. Philips Corporation, New York, N.Y.

[21] Appl. No.: 08/880,375

[22] Filed: Jun. 23, 1997

[30] Foreign Application Priority Data

Jul. 12, 1996 [EP] European Pat. Off. .............. 96201975

[51] Int. Cl.⁶ ................................... A47B 13/00
[52] U.S. Cl. .............................. 5/601; 324/318; 600/410; 600/415
[58] Field of Search ..................... 600/410, 415, 600/407, 425; 5/601; 324/318, 322; 128/845; 252/62.51

[56] References Cited

U.S. PATENT DOCUMENTS

| | | | |
|---|---|---|---|
| 3,833,951 | 9/1974 | Nurwitz | 5/698 |
| 5,014,968 | 5/1991 | Lammers et al. | 269/322 |
| 5,285,160 | 2/1994 | Loos et al. | 324/318 |
| 5,416,413 | 5/1995 | Leussler | 324/318 |
| 5,728,079 | 3/1998 | Weber et al. | 604/280 |

OTHER PUBLICATIONS

Multinuclear NMR Investigations of Probe Construction Materials at 4.7T, Magnetic Resonance in Medicine 13, 498–503 (1990), E.E. Babcock, J.T. Vaughan, B. Lesan and R.L. Nunnally.

*Primary Examiner*—Ruth S. Smith
*Attorney, Agent, or Firm*—Dwight H. Renfrew, Jr.

[57] ABSTRACT

Magnetic resonance apparatus includes an examination zone (29) for receiving an object (37) to be examined, a component (41) of an electrically non-conductive plastic material being located in the examination zone at least when the apparatus is in an operating condition. In order to reduce the visibility of this component (41) in MR experiments, the plastic material contains an additive of a paramagnetic material.

12 Claims, 3 Drawing Sheets

COMPONENTS OF A PLASTIC MATERIAL FOR USE IN A MAGNETIC RESONANCE APPARATUS

BACKGROUND OF THE INVENTION

1. Field of the Invention

The invention relates to a magnetic resonance examination apparatus, comprising an examination zone for receiving an object to be examined, a component of an electrically non-conductive plastic material being located in the examination zone at least when the apparatus is in an operating condition. The invention also relates to a patient table for use in an apparatus of this kind.

2. Description of the Related Art

An apparatus of this kind is known from U.S. Pat. No. 5,416,413). The known apparatus comprises a support for a coil system, the support being made of a non-conductive synthetic (plastic) material. When the apparatus is in operation, the support is located in an examination zone in which a strong, uniform magnetic field, gradient magnetic fields and an RF magnetic field are generated. Thus, the apparatus can be used e.g. for magnetic resonance (MR) imaging or spectroscopy of an object to be placed in the examination zone. It has been found that in some experiments plastic parts become visible or give artefacts in unknown and unpredictable locations in the images and spectra. Results of an investigation of this phenomenon have been published in Magnetic Resonance in Medicine, 13, 498–503 (1990). From this publication it is clear that many materials which, from the point of view of dielectric properties and/or machinability, would be very suitable for manufacturing components to be used in the examination zone cannot be used because they become visible or give artefacts as mentioned above.

SUMMARY OF THE INVENTION

It is, therefore, an object of the invention to provide an apparatus of the kind set forth, which provides a greater freedom of choice of plastic materials for the manufacture of components than the known apparatus. The apparatus in accordance with the invention is characterized in that the plastics material comprises an additive of a paramagnetic material. The invention is based on the following insight: Many plastic materials comprise free protons that are detectable with MR. Adding a slight amount of a paramagnetic material will cause local disturbances in the magnetic field experienced by these free protons thereby substantially reducing the detectability of these protons.

It has been found that good results are obtained if the amount of paramagnetic material in the plastic material is between 0.5% and 10% by weight. All paramagnetic materials are suitable but best results have been obtained with manganese and bismuth. Suitable plastic materials are the polymers, a good example being polyurethane which showed a considerable improvement when a paramagnetic material was added to it.

These and other aspects of the invention will be apparent from the embodiments described hereinafter.

DETAILED DESCRIPTION OF THE PREFERRED EMBODIMENTS

Figure 1:
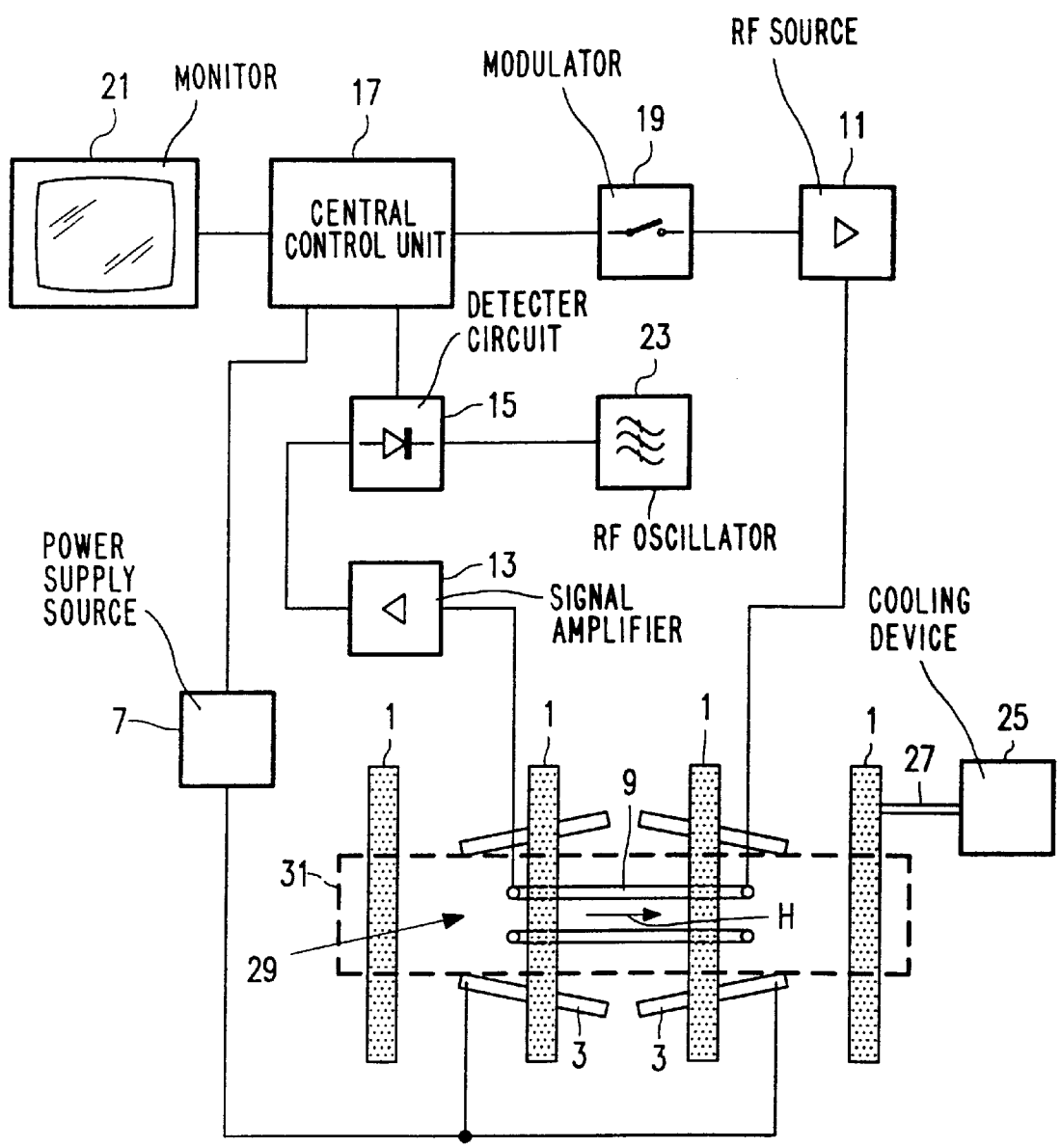
FIG. 1 shows a block diagram of an embodiment of a magnetic resonance examination apparatus in accordance with the invention.

The MR apparatus which is diagrammatically shown in FIG. 1 comprises a first magnet system 1 for generating a steady magnetic field H, a second magnet system 3 for generating magnetic gradient fields, and a power supply source 7 for the second magnet system 3. A radio frequency (RF) coil 9 serves to generate an RF magnetic alternating field; to this end, it is connected to an RF source 11. The RF coil 9 can also be used for detection of spin resonance signals generated by the RF transmitted field in an object to be examined (not shown); to this end, it is connected to an RF receiver device comprising a signal amplifier 13. The output of the signal amplifier 13 is connected to a detector circuit 15 which is connected to a central control unit 17. The central control unit 17 also controls a modulator 19 for supplying a modulated RF signal to the RF source 11, controls the power supply source 7, and generates a display signal which is supplied to a monitor 21. An RF oscillator 23 feeds the modulator 19 as well as the detector circuit 15 which detects the measurement signals. For cooling of the magnet coils of the first magnet system 1 there is provided a cooling device 25 comprising cooling ducts 27. The RF coil 9, arranged within the magnet systems 1 and 3, encloses a measurement space or examination zone 29 which is large enough to accommodate a patient to be examined, or a part of a patient to be examined, for example the head and the neck, in an apparatus for medical diagnostic measurements. Thus, a steady magnetic field H, gradient fields selecting object slices, and a spatially uniform RF alternating field can be generated within the examination zone 29. The RF coil 9 can combine the functions of transmitter coil and measuring coil. Alternatively, different coils can be used for the two functions, for example measuring coils in the form of surface coils. If desired, the coil 9 may be enclosed by an RF field shielding Faraday cage 31.

Figure 2:
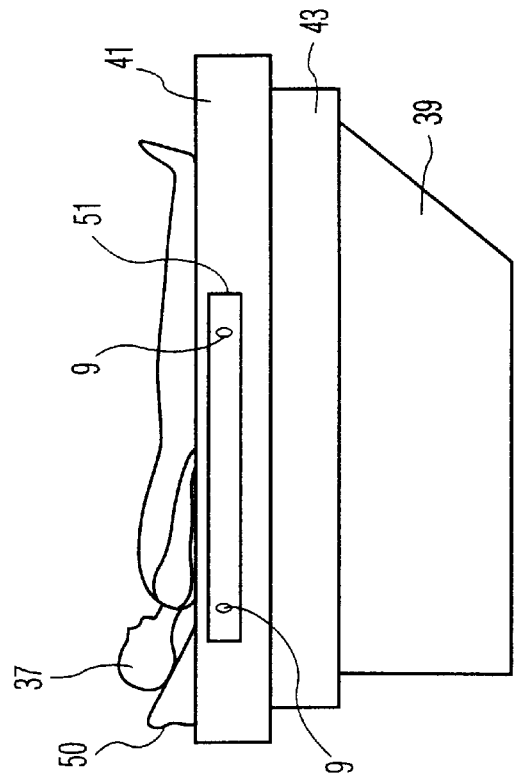
FIG. 2 shows a side elevation of the apparatus shown in FIG. 1.
Figure 2:
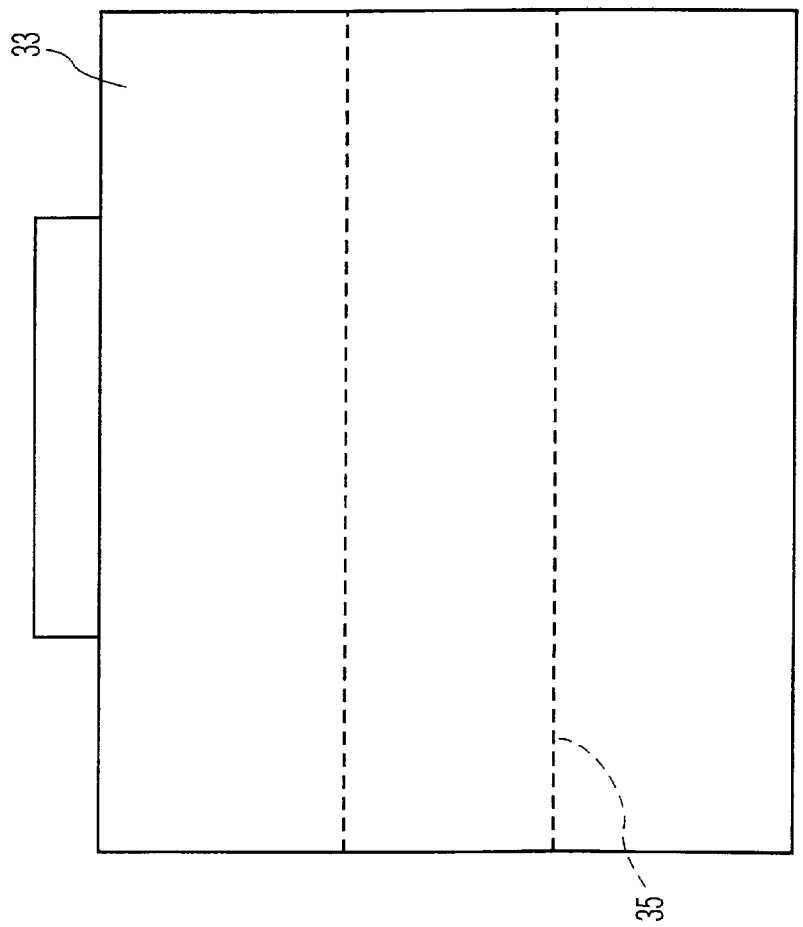

FIG. 2 is a side elevation of the apparatus shown diagrammatically in FIG. 1. The magnet systems 1 and 3 are located in a housing 33 that comprises a circular cylindrical bore 35 (shown in dotted lines) for receiving a patient 37. The patient 37 lies on a patient table 39, comprising a detachable table top 41 which is displaceable in a longitudinal direction (parallel to the cylinder axis of the bore 35) on a support 43. The table top with the patient lying on it can be slid into the bore 35. This construction is described in detail in U.S. Pat. No. 5,014,968. The table top 41 is made of an electrically non-conductive material, usually a plastic material. Further parts, for example a housing 51 accommodating the RF coil 9 and a head rest 50 for supporting the head of the patient 37, may be located on the table top 41. An example of such parts is described in detail in U.S. Pat. No. 5,285,160. These parts too are usually made of a suitable plastic material.

An example of a plastic material that meets the requirements of machinability and dielectric properties is polyurethane. However, the cited article in Magnetic Resonance in Medicine 13, 498–503 discloses that this material gives an unacceptably high MR signal for protons. It is believed that this is caused by the presence of free protons in the polyurethane. Components of this material are formed by simultaneously injecting, for example, a polyol and C-isocyanate in a mould. These two chemicals will form long intertwining strings.

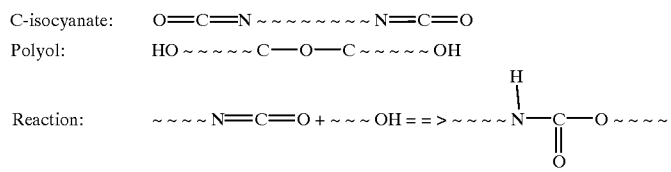

In reactions like this one, not all the OH-groups will be gone after the reaction. The remaining OH-groups comprise 'free' protons which will be detectable with MR. They have T2 relaxation times in the order of 20 ms. It has been found that adding a slight amount of a paramagnetic material such as manganese or bismuth will cause local disturbances of the magnetic field at the location of the free protons, thereby causing a decrease of the T2*. This substantially reduces the detectability of these free protons.

Figure 3:
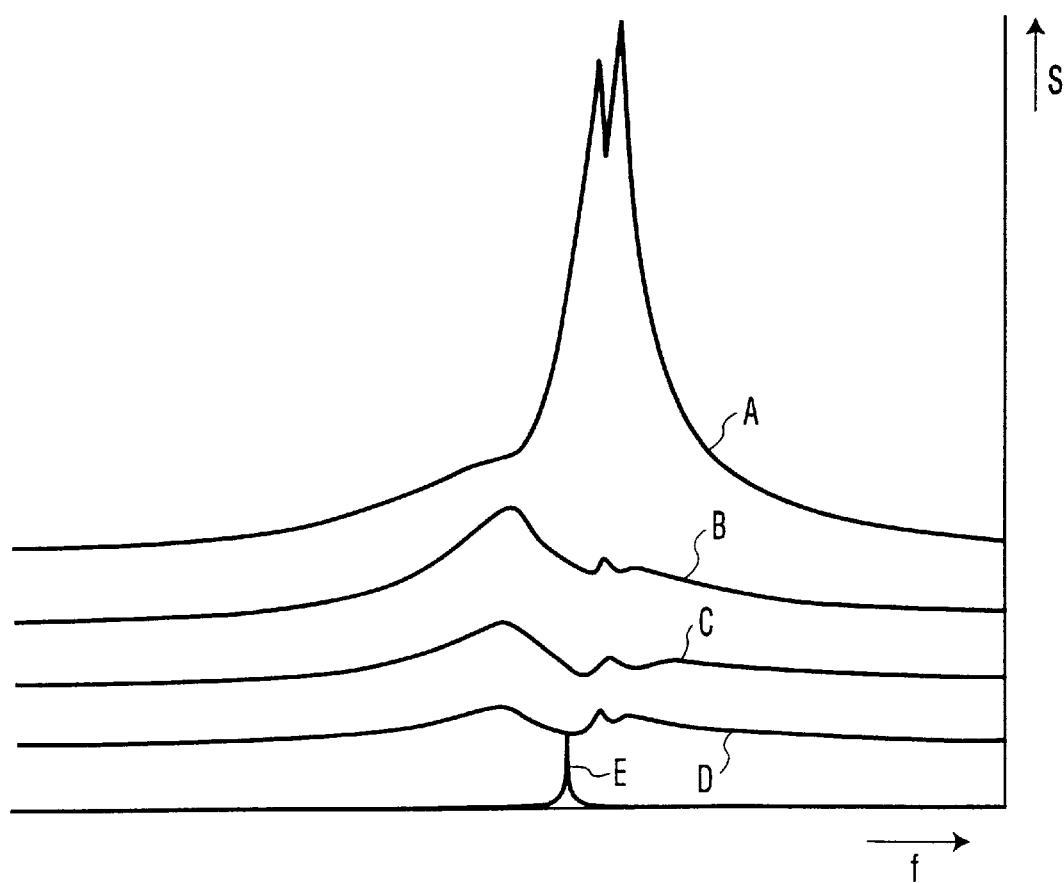
FIG. 3 shows a diagram illustrating the improvements obtained with the invention.

For testing purposes, a small production unit with a rectangular mould (25×15×1 cm) was put into service to produce test samples with a density similar to that of actual coil parts. In the supply bins the polyol was mixed with a predetermined amount of $MnSO_4(+1H_2O)$. Samples with different concentrations of $Mn^+$ were made, one of these samples (sample A) consisting of the basic material (polyurethane), another (sample B) consisting of the basic material and an additive of 5% (weight) $MnSO_4=1H_2O$ and a third sample (sample C) consisting of the basic material and 10% (weight) of the same additive. By chemical analysis of the samples, the concentrations of $Mn^+$ in samples B and C were determined to be about 1.5% and 6.6% by weight, respectively. The proton MR spectra of the samples were measured in an MR apparatus. The result is shown in the diagram of FIG. 3.

The diagram shows the signal s obtained from each one of the samples A, B and C as a function of the frequency f. The curve marked D shows the signal obtained from the 'empty' MR apparatus (the apparatus without any sample) and the curve marked E shows the signal obtained from a sample of 10 ml $H_2O$ as a reference. For the sake of clarity, the curves A, B, C and D have been shifted in the vertical direction to prevent them from overlapping. In reality, the curve C is, within the measuring accuracy coincident with the curve D. The peak of curve B is about three times as high of the peak of curve C and the peak of curve A is about six times as high as the peak of curve B. From this it is clear that the addition of a paramagnetic material to a plastic material significantly reduces the visibility in MR experiments of parts made from that material.

After these successful tests the addition of manganese to polyurethane was used in the normal production of under covers for head coils. Because $MnSO_4$ is available for laboratory use only (it is rather expensive), it was decided to use $MnCO_3$ which is available in bulk. Covers were made from polyurethane with this additive and chemical analysis of one of these covers showed the actual concentration of $Mn^+$ to be 0.67%. When the proton signal of these covers was measured in an MR apparatus, it turned out to be a factor 5 less than the signal from a standard cover from polyurethane without a paramagnetic additive. From these and other experiments it follows that good results are obtained when the amount of paramagnetic material in the plastic material is between 0.5% and 10% by weight.

All references cited herein are incorporated herein by reference in their entirety and for all purposes to the same extent as if each individual publication or patent or patent application was specifically and individually indicated to be incorporated by reference in its entirety for all purposes.

I claim:

1. A patient table for use in a magnetic resonance examination apparatus, the table comprising a table top of an electrically non-conductive plastic material, wherein the plastic material comprises an additive of a paramagnetic material in an amount between 0.5% and 10% by weight which substantially reduces the detectability of the table top when used in a magnetic resonance apparatus.

2. A patient table as claimed in claim 1 wherein the paramagnetic material is manganese or bismuth.

3. A patient table as claimed in claim 2 wherein the plastic material is a ploymer.

4. A patient table as claimed in claim 1 wherein the plastic material is a polymer.

5. The patient table of claim 1 further comprising a head rest of an electrically non-conductive plastic material, wherein the head rest is configured and sized to support a head of a patient and is positioned on the table top, and wherein the electrically non-conductive plastic material comprises an additive of a paramagnetic material which substantially reduces the detectability of the head rest when used in a magnetic resonance apparatus.

6. The patient table of claim 1 further comprising a housing for a radio-frequency (RF) coil of an electrically non-conductive plastic material, wherein the housing is configured and sized to enclose an RF coil and is supported by the table top, and wherein the electrically non-conductive plastic material comprises an additive of a paramagnetic material which substantially reduces the detectability of the housing.

7. A patient table for use in a magnetic resonance apparatus comprising:

a table top for supporting a patient, and a head rest of an electrically non-conductive plastic material, wherein the head rest is configured and sized to support a head of the patient and is positioned on the table top, and wherein the electrically non-conductive plastic material comprises an additive of a paramagnetic material in an amount between 0.5% and 10% by weight which substantially reduces the detectability of the head rest when used in a magnetic resonance apparatus.

8. The table of claim 7 wherein the paramagnetic material is manganese or bismuth.

9. The table of claim 7 wherein the plastic material is a polymer.

10. An radio-frequency (RF) coil assembly for use in a magnetic resonance examination apparatus comprising:

an RF coil, and a housing for the RF coil of an electrically non-conductive plastic material, wherein the housing is configured and sized to enclose the RF coil, and wherein the electrically non-conductive plastic material comprises an additive of a paramagnetic material in an amount between 0.5% and 10% by weight which substantially reduces the detectability of the housing when used in a magnetic resonance apparatus.

11. The assembly of claim 10 wherein the paramagnetic material is manganese or bismuth.

12. The assembly claim 10 wherein the plastic material is a polymer.

* * * * *